United States Patent
Patel et al.

(10) Patent No.: US 12,303,504 B2
(45) Date of Patent: May 20, 2025

(54) NON-AQUEOUS CHEMOTHERAPEUTIC SUSPENSIONS FOR ORAL DOSAGE

(71) Applicant: ONCOSOL LIMITED, Weedon (GB)

(72) Inventors: Vijay Patel, Ahmedabad (IN); Sandip Mehta, Ahmedabad (IN); Manish Kumar Umrethia, Ahmedabad (IN); Jayanta Mandal, Ahmedabad (IN)

(73) Assignee: ONCOSOL LIMITED, Weedon (GB)

( * ) Notice: Subject to any disclaimer, the term of this patent is extended or adjusted under 35 U.S.C. 154(b) by 740 days.

(21) Appl. No.: 17/274,432

(22) PCT Filed: Sep. 13, 2019

(86) PCT No.: PCT/IB2019/001044
§ 371 (c)(1),
(2) Date: Mar. 9, 2021

(87) PCT Pub. No.: WO2020/053665
PCT Pub. Date: Mar. 19, 2020

(65) Prior Publication Data
US 2023/0158018 A1   May 25, 2023

(30) Foreign Application Priority Data
Sep. 13, 2018 (IN) .............................. 201821034590

(51) Int. Cl.
| | |
|---|---|
| *A61K 31/495* | (2006.01) |
| *A61K 9/00* | (2006.01) |
| *A61K 9/10* | (2006.01) |
| *A61K 31/454* | (2006.01) |
| *A61K 47/02* | (2006.01) |
| *A61K 47/10* | (2017.01) |
| *A61K 47/14* | (2017.01) |

(52) U.S. Cl.
CPC .......... *A61K 31/495* (2013.01); *A61K 9/0053* (2013.01); *A61K 9/10* (2013.01); *A61K 31/454* (2013.01); *A61K 47/02* (2013.01); *A61K 47/10* (2013.01); *A61K 47/14* (2013.01)

(58) Field of Classification Search
None
See application file for complete search history.

(56) References Cited

U.S. PATENT DOCUMENTS

| | | | | |
|---|---|---|---|---|
| 3,920,819 | A * | 11/1975 | Stephens | A61K 9/0095 514/777 |
| 2011/0301177 | A1 * | 12/2011 | Messerschmid | A61K 9/4858 206/524.6 |
| 2013/0115294 | A1 * | 5/2013 | First | A61K 31/4439 424/490 |

FOREIGN PATENT DOCUMENTS

| | | | | |
|---|---|---|---|---|
| WO | WO-9956727 A2 * | 11/1999 | ........... | A61K 9/1075 |
| WO | 2010061209 A1 | 6/2010 | | |
| WO | 2018167627 A1 | 9/2018 | | |
| WO | WO-2020039264 A2 * | 2/2020 | ........... | A61K 31/404 |

OTHER PUBLICATIONS

Jin L, Yang YZ, Fan JF, Xu BS. Effect of Surfactant Polyvinyl Pyrrolidone on the Properties of Microporous Carbon Nanospheres Reinforced Magnesium Matrix Composites. Nanomaterials (Basel). Nov. 17, 2020;10(11):2281. (Year: 2020).*
Jadhav HB, Annapure US. Triglycerides of medium-chain fatty acids: a concise review. J Food Sci Technol. Aug. 2023;60(8):2143-2152. doi: 10.1007/s13197-022-05499-w. Epub Jun. 22, 2022. PMID: 35761969; PMCID: PMC9217113. (Year: 2023).*
Song et al. Improving the Solubility of Lenalidomide via Cocrystals. Crystal Growth & Design. Published May 7, 2014. (Year: 2014).*
Ronak Savla, Jeff Browne, Vincent Plassat, Kishor M. Wasan & Ellen K. Wasan (2017) Review and analysis of FDA approved drugs using lipid-based formulations, Drug Development and Industrial Pharmacy, 43:11, 1743-1758, DOI: 10.1080/03639045.2017.1342654 (Year: 2017).*
Chen et al. Clinical Pharmacokinetics and Pharmacodynamics and Lenalidomide. Clin Pharmacokinet (2017) 56:139-152. (Year: 2017).*
Ataman Chemicals. Span 60. Retrieved from the Internet on Sep. 17, 2024, https://www.atamanchemicals.com/span-60_u26797/#:~:text=Span%2060%20is%20primarily%20used,detergents%2C%20spreading%20or%20dispersing%20agents . . . (Year: 2024).*
Becker. Final report on the amended safety assessment of Propyl Gallate. Int J Toxicol. 2007;26 Suppl 3:89-118. doi: 10.1080/10915810701663176. PMID: 18080874. (Year: 2007).*
Chen et al., Pharmacokinetics, metabolism and excretion of [14C]-lenalidomide following oral administration in healthy male subjects, Cancer Chemotherapy and Pharmacology (2012) 69(3): 789-797.
Chen et al., Clinical Pharmacokinetics and Pharmacodynamics of Lenalidomide, Clinical Pharmacokinetics (2017) 56(2): 139-152.
Morita et al., Stability of lenalidomide suspension after preparation by a simple suspension method for enteral tube administration, Journal of Oncology Pharmacy Practice (2015) 22(4): 579-583.
Revlimid (lenalidomide) capsules, Prescribing Information as of Dec. 29, 2017, 46 pp.

(Continued)

*Primary Examiner* — James H Alstrum-Acevedo
*Assistant Examiner* — Lauren Wells
(74) *Attorney, Agent, or Firm* — Merchant & Gould P.C.; Daniel R. Evans; Daniel J. Pereira

(57) ABSTRACT

Pharmaceutical compositions comprising oil as a vehicle, a suspending agent, and a surfactant are disclosed to be used in conjunction with active pharmaceutical ingredients which are water soluble or insoluble, or which are sensitive to water but insoluble in oil. Such active pharmaceutical ingredients may include temozolomide, lenalidomide, Oxaliplatin, Cisplatin, Carboplatin, 5-fluorouracil, irinotecan, topotecan, cyclophosphamide, doxorubicin, vincristine, vinblastine, Melphalan, Chlorambucil, Dacarbazine, Daunorubicin, Epirubicin, Mitoxantrone, Etoposide, Teniposide, Azacitidine, Cytarabine, Gemcitabine, vinoralbine, Pemetrexed, a derivative thereof, or a combination thereof. The pharmaceutical compositions may be administered as an oral suspension. Other embodiments are directed towards methods of using and methods of making such formulations.

14 Claims, No Drawings

(56) References Cited

OTHER PUBLICATIONS

Fotios Ambados et al, "Preparation Method and Stability of a Temozolomide Suspension: A Pilot Study", Journal of Pharmacy Practice and Research, vol. 42, No. 2, Jun. 13, 2012 (Jun. 13, 2012), pp. 111-114, XP055365602, AU ISSN: 1445-937X, DOI:10.1002/j.2055-2335.2012.tb00145.x.

* cited by examiner

NON-AQUEOUS CHEMOTHERAPEUTIC SUSPENSIONS FOR ORAL DOSAGE

PRIORITY

This application is the U.S. national stage application of PCT/IB2019/001044, filed on Sep. 13, 2019, which claims priority to Indian Provisional Application No. IN201821034590 filed on Sep. 13, 2018, which is incorporated herein by reference.

SUMMARY

Embodiments herein are directed to a pharmaceutical composition in the form of a liquid suspension for active pharmaceutical ingredients that are soluble in water, insoluble in water, or sensitive to water and which are insoluble in oil. In some embodiments, the suspension comprises an active pharmaceutical ingredient which is soluble, insoluble, or sensitive to water, a vehicle, a surfactant, and a suspending agent. In some embodiments, the active pharmaceutical ingredient is a chemotherapeutic active pharmaceutical ingredient. In some embodiments, the active pharmaceutical ingredient may be selected from temozolomide, lenalidomide, Oxaliplatin, Cisplatin, Carboplatin, 5-fluorouracil, irinotecan, topotecan, cyclophosphamide, doxorubicin, vincristine, vinblastine, Melphalan, Chlorambucil, Dacarbazine, Daunorubicin, Epirubicin, Mitoxantrone, Etoposide, Teniposide, Azacitidine, Cytarabine, Gemcitabine, vinoralbine, Pemetrexed, a derivative thereof, or a combination thereof. In some embodiments, the pharmaceutical composition does not include a non-chemotherapeutic active pharmaceutical ingredient. In some embodiments, the pharmaceutical composition does not include a non-chemotherapeutic active pharmaceutical ingredient which is soluble in water, insoluble in water, or sensitive to water.

In some embodiments, the vehicle may be an oil. In some embodiments, the vehicle may be a medium chain fatty acid. In some embodiments, the medium chain fatty acid may be any fatty acid having from 6 to 12 carbon atoms. For example, the medium chain fatty acid may be selected from caproic acid (C6), caprylic acid (C8), capric acid (C10), lauric acid (C12), coconut oilarachis oil, soya bean oil, castor oil, corn oil, safflower oil, olive oil, apricot kernel oil, sesame oil, cotton seed oil, sunflower seed oil, palm oil, rapeseed oil, mineral oil, or a combination thereof. In some embodiments, the medium chain fatty acid may be selected from caproic triglyceride, caprylic triglyceride, capric triglyceride, lauric triglyceride, or a combination thereof. In some embodiments, the medium chain fatty acid is found in medium-chain triglycerides (MCTs), which are medium-chain (6 to 12 carbons) fatty acid esters of glycerol. Examples of MCTs which may be used in embodiments herein include MIGLYOL, made from various distillation fractions of coconut oil, palm kernel oil, camphor tree drupes, or combinations thereof. In some embodiments, the oil is Kollisolv MCT 70.

In some embodiments, the surfactant may be sorbitan esters (Span), especially from saturated or unsaturated fatty acids, polyethoxylated sorbitan esters (Tween), especially from saturated or unsaturated fatty acids, Caprylocaproyl macrogol-8 glycerides (Labrasol), Lauroyl macrogol-32 glycerides (Gelucire 44/14), stearoyl macrogol-32 glycerides (Gelucire 50/13), especially from saturated or unsaturated fatty acids, polyethoxylated and/or hydroginated castor oils such as PEG-40 hydrogenated castor oil (Cremophor RH 40®), PEG-60 hydrogenated castor oil (Cremophor RH 60®), PEG-35 castor oil or polyoxyl 35 castor oil (Cremophor EL), Macrogol (25) cetostearyl ether (Cremophor A25), polyethoxylated ethers, especially from saturated or unsaturated fatty alcohols, polyethylene glycol such as PEG 200, poloxamer (Lutrol F 127), alpha tocopherol, polyoxyethylene lauryl ether (Brji 30, Brji 35), polyvinyl caprolactam-polyvinylacetate-polyethyleneglycol graft copolymer (e.g. Soluplus®), PEG-35 castor oil, or a combination thereof.

In some embodiments, the suspending agent may be selected from the group consisting of gelatin, colloidal silica, crosslinked polyacrylic acid, polymethacrylic acid, polyhydroxyethyl methacrylic acid, hydroxypropyl methyl cellulose, sodium carboxymethyl cellulose, hyaluronic acid, chitosan, polycarbophil, pectin, copolymers of dextran, polyacrylamide, acacia, copolymer of caprolactone and ethylene oxide, carbopol 934, tragacanth, eudragit, polyvinyl pyrrolidone, polyacrylate and polyacrylate copolymer resins, celluloses and cellulose derivatives for example methyl-, ethyl- and propyl celluloses; hydroxyalkyl-celluloses, hydroxyl propyl celluloses, hydroxylpropylalkyl celluloses and the like including xanthan gum, polyvinyl resins, polyethylene glycol, polyethylene oxide, sorbitol, sucrose, xylitol, dextrose, fructose, maltitol, sugar, sodium alginate, and a combination thereof.

In some embodiments, the pharmaceutical composition may further comprise a solubilizer, an antioxidant, a sweetener, a flavoring agent, a buffering agent, a sweetness/flavor enhancing agent, a chelating agent, a preservative, or any combination thereof.

Some embodiments are directed to a methods of using the pharmaceutical composition of embodiments herein for the treatment of diseases or disorders. In some embodiments, the disease or disorder comprises cancer, multiple myeloma, cancers of the blood, myelodysplastic syndrome, Hodgkin's lymphoma, non-Hodgkin's lymphoma, chronic lymphosytic leukemia, solid tumor cancers, carcinoma of the pancreas, B-cell chronic lymphocytic leukemia, or a combination thereof, wherein the active pharmaceutical ingredient is lenalidomide.

In some embodiments, the disease or disorder comprises cancer, brain cancer, astrocytoma, glioblastoma, glioblastoma multiforme, anaplastic astrocytoma, melanoma, brain metastasis, brain metastasis of breast cancer, or a combination thereof, wherein the active pharmaceutical ingredient is temozolomide.

In some embodiments, a method of treating multiple myeloma in a subject in need thereof comprises administering to the subject the pharmaceutical composition of embodiments herein, wherein the active pharmaceutical ingredient is lenalidomide.

In some embodiments, a method of treating a myelodysplastic syndrome in a subject in need thereof comprises administering to the subject the pharmaceutical composition of embodiments herein, wherein the active pharmaceutical ingredient is lenalidomide.

In some embodiments, a method of treating astrocytoma in a subject in need thereof comprises administering to the subject the pharmaceutical composition of embodiments herein, wherein the active pharmaceutical ingredient is temozolomide.

In some embodiments, a method of treating glioblastoma multiforme in a subject in need thereof comprises administering to the subject the pharmaceutical composition of embodiments herein, wherein the active pharmaceutical ingredient is temozolomide.

In some embodiments, the suspension comprises about 0.1% w/w to about 50% w/w of the active agent, about 0.01% w/w to about 10% w/w surfactant, about 0.1% w/w to about 20% w/w suspending agent, and about 0.1% w/w to about 95% w/w vehicle. In some embodiments, the suspension comprises about 0.1% w/w to about 50% w/w of the active agent, about 0.01% w/w to about 10% w/w surfactant, about 0.1% w/w to about 20% w/w suspending agent, and about 0.1% w/w to about 95% w/w medium chain triglyceride. In some embodiments, the suspension comprises about 0.1% w/w to about 50% w/w of temozolomide, about 0.01% w/w to about 10% w/w surfactant, about 0.1% w/w to about 20% w/w suspending agent, and about 0.1% w/w to about 95% w/w medium chain triglyceride. In some embodiments, the suspension comprises about 0.1% w/w to about 50% w/w of lenalidomide, about 0.01% w/w to about 10% w/w surfactant, about 0.1% w/w to about 20% w/w suspending agent, and about 0.1% w/w to about 95% w/w medium chain triglyceride.

DETAILED DESCRIPTION

Before the present compositions and methods are described, it is to be understood that this invention is not limited to the particular processes, formulations, compositions, or methodologies described, as these may vary. It is also to be understood that the terminology used in the description is for the purpose of describing the particular versions or embodiments only, and is not intended to limit the scope of embodiments herein which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of embodiments herein, the preferred methods, devices, and materials are now described. All publications mentioned herein are incorporated by reference in their entirety. Nothing herein is to be construed as an admission that embodiments herein is not entitled to antedate such disclosure by virtue of prior invention.

It must also be noted that as used herein and in the appended claims, the singular forms "a," "an," and "the" include plural reference unless the context clearly dictates otherwise. Thus, for example, reference to a "surfactant" is a reference to one or more surfactants and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with an active pharmaceutical ingredient, can include, but is not limited to, providing the active pharmaceutical ingredient into or onto the target tissue; providing the active pharmaceutical ingredient systemically to a patient by, e.g., intravenous injection whereby the therapeutic reaches the target tissue; providing the active pharmaceutical ingredient in the form of the encoding sequence thereof to the target tissue (e.g., by so-called gene-therapy techniques). "Administering" a composition may be accomplished by injection, topical administration, orally, or by either method in combination with other known techniques. In some embodiments, administering is through an oral route of administration.

The term "subject" as used herein includes, but is not limited to, humans and non-human vertebrates such as wild, domestic, and farm animals. In certain embodiments, the subject described herein is an animal. In certain embodiments, the subject is a mammal. In certain embodiments, the subject is a human. In certain embodiments, the subject is a non-human animal. In certain embodiments, the subject is a non-human mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

The term "improve" is used to convey that the compounds of embodiments herein change either the appearance, form, characteristics and/or the physical attributes of the tissue to which it is being provided, applied or administered. In some embodiments, the pharmaceutical compositions of embodiments herein comprising temozolomide are suited to improve the outcome of patients having astrocytoma.

The term "inhibit" includes the administration of a compound of embodiments herein to prevent the onset of the symptoms, alleviating the symptoms, or eliminating the disease, condition or disorder. In some embodiments, the pharmaceutical compositions of embodiments herein comprising temozolomide are suited to inhibit the symptoms of metastatic castrate-resistant prostate cancer.

The term "pharmaceutically acceptable" as used herein means that which is useful in preparing a pharmaceutical composition that is generally non-toxic and is not biologically undesirable and includes that which is acceptable for human use and/or veterinary use.

The term "compatible" as used herein refers to those added excipients or ingredients or additives that are not substantially antagonistic to the other excipients or ingredients or additives or pharmaceutically active ingredients.

The term "chemotherapeutic", as used herein, refers to compounds, compositions, and/or therapies which are used in the treatment of cancer or which are anti-neoplastic.

The term "non-chemotherapeutic", as used herein, refers to compounds, compositions, and/or therapies which are not used in the treatment of cancer and which are not anti-neoplastic.

As used herein, the term "therapeutic" means an agent utilized to treat, combat, inhibit, ameliorate, prevent or improve an unwanted condition or disease of a patient. In part, embodiments of embodiments herein are directed to the treatment of metastatic castrate-resistant prostate cancer.

A "therapeutically effective amount" or "effective amount" of a composition is a predetermined amount calculated to achieve the desired effect. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, concomitant therapies and the condition being treated. However, it will be understood that the effective amount administered will be determined by the physician in the light of the relevant circumstances including the condition to be treated, the choice of compound to be administered, and the chosen route of administration, and therefore the above dosage ranges are not intended to limit the scope of embodiments herein in any way. A therapeutically effective amount of a compound of this disclosure is typically an amount such that when it is administered in a physiologically tolerable excipient composition, it is sufficient to achieve an effective systemic concentration or local concentration in the tissue.

The terms "treat," "treated," or "treating," as used herein, refers to both therapeutic treatment and prophylactic or preventative measures, wherein the object is to inhibit, prevent or slow down (lessen) an undesired physiological condition, disorder or disease, or to improve, inhibit, or otherwise obtain beneficial or desired clinical results. For the purposes of this invention, beneficial or desired clinical results include, but are not limited to, improvement or alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

As used herein, the term "a derivative thereof" refers to a salt thereof, a pharmaceutically acceptable salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof. In some embodiments, the active pharmaceutical ingredient may be administered as a derivative thereof.

In embodiments or claims where the term "comprising" is used as the transition phrase, such embodiments can also be envisioned with replacement of the term "comprising" with the terms "consisting of" or "consisting essentially of."

As used herein, the term "consists of" or "consisting of" means that the composition, formulation or the method includes only the elements, steps, or ingredients specifically recited in the particular claimed embodiment or claim.

As used herein, the term "consisting essentially of" or "consists essentially of" means that the composition, formulation or the method includes only the elements, steps or ingredients specifically recited in the particular claimed embodiment or claim and may optionally include additional elements, steps or ingredients that do not materially affect the basic and novel characteristics of the particular embodiment or claim. For example, the only active pharmaceutical ingredient(s) in the formulation or method that treats the specified condition (e.g. prostate cancer) is the specifically recited therapeutic(s) in the particular embodiment or claim.

Temozolomide is known for its alkylating antitumor effects. Temozolomide is approved as a second-line treatment for astrocytoma and a first-line treatment for glioblastoma multiforme. This compound works by alkylating DNA, typically through addition of a methyl group to guanine in genomic DNA that leads to arrest at the G2/M cell cycle and triggers the death of tumor cells.

Temozolomide is available in the market under the brand names Temodar or Temodal in hard capsule dosage form containing 5 mg, 20 mg, 100 mg or 250 mg Temozolomide. In capsule formulation of Temozolomide, the active ingredient is contained at a high dosage per capsule, so it is difficult to achieve the full and uniform content. Further, it might be difficult to swallow solid dosage of the drug for all patients. Temozolomide is a prodrug and is rapidly hydrolyzed into 5-(3-methyltriazen-1-yl imidazole-4-carboxamide (MTIC) at neutral and alkaline pH values. This molecule further gets hydrolyzed at acidic pH (<5), hence it is available as a lyophilized powder for injection in market.

Embodiments herein are directed to a pharmaceutical composition for active pharmaceutical ingredients which are soluble in water, insoluble in water, or sensitive to water, and which are insoluble in oil. In some embodiments, the pharmaceutical composition is a solution. In some embodiments, the pharmaceutical composition is an oral solution. In some embodiments, the solution comprises an active pharmaceutical ingredient which is soluble in water, insoluble in water, or sensitive to water, an oil, a surfactant, and a solubilizer. In some embodiments, the pharmaceutical composition of embodiments herein does not include a non-chemotherapeutic active pharmaceutical ingredient. In some embodiments, the active pharmaceutical ingredient is a chemotherapeutic pharmaceutical ingredient.

In some embodiments, the active pharmaceutical ingredient may be selected from temozolomide, lenalidomide, Oxaliplatin, Cisplatin, Carboplatin, 5-fluorouracil, irinotecan, topotecan, cyclophosphamide, doxorubicin, vincristine, vinblastine, Melphalan, Chlorambucil, Dacarbazine, Daunorubicin, Epirubicin, Mitoxantrone, Etoposide, Teniposide, Azacitidine, Cytarabine, Gemcitabine, vinoralbine, Pemetrexed, a derivative thereof, or a combination thereof. In some embodiments, the active pharmaceutical ingredient water soluble, insoluble, or sensitive to water. The definition of solubility is as per the United States Pharmacopoeia as shown below in Table 1:

TABLE 1

| SOLUBILITY | |
| --- | --- |
| Term | Mass parts of solvent required to dissolve 1 mass part of solute |
| Very soluble | <1 |
| Freely soluble | 1 to 10 |
| Soluble | 10 to 30 |
| Sparingly soluble | 30 to 100 |
| Slightly soluble | 100 to 1000 |
| Very slightly soluble | 1000 to 10,000 |
| Practically insoluble or insoluble | ≥10,000 |

Alternatively, according to the Biopharmaceutics Classification System (BCS), a drug is considered to be poorly water-soluble if its highest dose strength is not soluble in 250 mL or less of aqueous media over the pH range of 1 to 7.5. In some embodiments, the pharmaceutical composition may be used with any BCS Class 2 or Class 4 chemotherapeutic agent. In some embodiments, the pharmaceutical composition may be used with any Biopharmaceutics Drug Disposition Classification System (BDDCS) Class 2 or Class 4 chemotherapeutic agent. Currently, 90% of orally administered drugs in clinical development are categorized as BCS/BDDCS II or IV and 40% fail because of insufficient biopharmaceutical properties such as poor drug solubility and sensitivity. This underlines the need for improved pharmaceutical formulations to deliver these therapeutics.

In some embodiments, the active pharmaceutical ingredient is in an amount of about 0.1 mg/mL, about 0.5 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, about 5 mg/mL, about 5.5 mg/mL, about 6 mg/mL, about 7 mg/mL, about 8 mg/mL, about 9 mg/mL, about 10 mg/mL, about 12 mg/mL, about 14 mg/mL, about 16 mg/mL, about 18 mg/mL, about 20 mg/mL, about 22 mg/mL, about 25 mg/mL, about 27 mg/mL, about 30 mg/mL, about 40 mg/mL, about 50 mg/mL, about 60 mg/mL, about 70 mg/mL, about 80 mg/mL, about 90 mg/mL, about 100 mg/mL, about 150 mg/mL, about 200 mg/mL, about 250 mg/mL, about 300 mg/mL, about 350 mg/mL, or a range of any two of these values.

In some embodiments, the active pharmaceutical ingredient is in an amount of about 0.01% w/w, 0.05% w/w, 0.1% w/w, 0.2% w/w, 0.3% w/w, 0.4% w/w, 0.5% w/w, 0.6% w/w, 0.7% w/w, 0.8% w/w, 0.9% w/w, about 1% w/w, about 3% w/w, about 5% w/w, about 10% w/w, about 15% w/w, about 20% w/w, about 25% w/w, about 30% w/w, about 35% w/w, about 40% w/w, about 45% w/w, about 50% w/w, about 55% w/w, or a range of any two of these values. In some embodiments, the active pharmaceutical ingredient is in an amount of about 0.01% w/w to about 20% w/w. In some embodiments, the active pharmaceutical ingredient is in an amount of about 0.01% w/w to about 10% w/w. In some embodiments, the active pharmaceutical ingredient is in an amount of about 0.01% w/w to about 5% w/w. In some embodiments, the active pharmaceutical ingredient is in an amount of about 3% w/w.

Vehicles of embodiments herein are the liquid bases which carry drug and other excipients in dissolved or dispersed state and may be selected from non-aqueous vehicles. Examples of suitable non-aqueous vehicles are but not limited to vegetable oils, mineral oils, organic oily bases or emulsified bases and triglycerides. In some embodiments, the vehicle is an oil. In some embodiments, the vehicle is medium chain triglyceride (e.g. that sold under the trade name Kollisolv® MCT 70).

Without intending to be limiting, it is believed that medium chain triglycerides exhibit excellent stabilization capability for alkylating agents which are sensitive to hydrolysis (e.g. temozolomide or lenalidomide).

In some embodiments, the vehicle is an oil. In some embodiments, the vehicle may be a medium chain fatty acid. In some embodiments, the medium chain fatty acid may be any fatty acid having from 6 to 12 carbon atoms. For example, the medium chain fatty acid may be selected from caproic acid (C6), caprylic acid (C8), capric acid (C10), lauric acid (C12), coconut oilarachis oil, soya bean oil, castor oil, corn oil, safflower oil, olive oil, apricot kernel oil, sesame oil, cotton seed oil, sunflower seed oil, palm oil, rapeseed oil, mineral oil, or a combination thereof. In some embodiments, the medium chain fatty acid may be selected from caproic triglyceride, caprylic triglyceride, capric triglyceride, lauric triglyceride, or a combination thereof. In some embodiments, the medium chain fatty acid is found in medium-chain triglycerides (MCTs), which are medium-chain (6 to 12 carbons) fatty acid esters of glycerol. Examples of MCTs which may be used in embodiments herein include MIGLYOL, made from various distillation fractions of coconut oil, Kollisolv, palm kernel oil, camphor tree drupes, or combinations thereof. In some embodiments, the oil is a vehicle and is added to the formulation at a quantum sufficit.

The vehicle may be in an amount of about 0.1% w/w, about 1% w/w, about 3% w/w, about 5% w/w, about 10% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w, about 85% w/w, about 90% w/w, about 93% w/w, about 94% w/w, about 95% w/w, about 99% w/w, or a range of any two of these values. In some embodiments, the vehicle may be in an amount of about 0.1% w/w to about 99% w/w. In some embodiments, the vehicle may be in an amount of about 3% w/w to about 95% w/w. In some embodiments, the vehicle may be in an amount of about 10% w/w to about 95% w/w. In some embodiments, the vehicle may be in an amount of about 90% w/w to about 95% w/w.

In some embodiments, the surfactant may be sorbitan esters (Span), especially from saturated or unsaturated fatty acids, polyethoxylated sorbitan esters (Tween), especially from saturated or unsaturated fatty acids, Caprylocaproyl macrogol-8 glycerides (Labrasol), Lauroyl macrogol-32 glycerides (Gelucire 44/14), stearoyl macrogol-32 glycerides (Gelucire 50/13), especially from saturated or unsaturated fatty acids, polyethoxylated and/or hydroginated castor oils such as PEG-40 hydrogenated castor oil (Cremophor RH 40®), PEG-60 hydrogenated castor oil (Cremophor RH 60®), PEG-35 castor oil or polyoxyl 35 castor oil (Cremophor EL), Macrogol (25) cetostearyl ether (Cremophor A25), polyethoxylated ethers, especially from saturated or unsaturated fatty alcohols, polyethylene glycol such as PEG 200, poloxamer (Lutrol F 127), alpha tocopherol, polyoxyethylene lauryl ether (Brji 30, Brji 35), polyvinyl caprolactam-polyvinylacetate-polyethyleneglycol graft copolymer (e.g. Soluplus®), PEG-35 castor oil, or a combination thereof.

In some embodiments, the surfactant is in the pharmaceutical composition in an amount of about 0.5 mg/mL, about 1 mg/mL, about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 100 mg/mL, about 150 mg/mL, about 200 mg/mL, about 250 mg/mL, about 300 mg/mL, about 350 mg/mL, about 400 mg/mL, about 450 mg/mL, about 500 mg/mL, about 550 mg/mL, about 600 mg/mL, about 650 mg/mL, about 700 mg/mL, about 750 mg/mL, or a range of any two of these values. In some embodiments, the surfactant is in the pharmaceutical composition in an amount of about 0.5 mg/mL to about 660 mg/mL. In some embodiments, the surfactant is in the pharmaceutical composition in an amount of about 1 mg/mL to about 660 mg/mL. In some embodiments, the surfactant is in the pharmaceutical composition in an amount of about 5 mg/mL to about 660 mg/mL. In some embodiments, the surfactant is in the pharmaceutical composition in an amount of about 30 mg/mL.

In some embodiments, the surfactant is in the pharmaceutical composition in an amount of about 0.01% w/w, about 0.1% w/w, about 0.5% w/w, about 1% w/w, about 2% w/w, about 3% w/w, about 4% w/w, about 5% w/w, about 6% w/w, about 7% w/w, about 8% w/w, about 9% w/w, about 10% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w, about 85% w/w, about 90% w/w, about 95% w/w, or a range of any two of these values. In some embodiments, the surfactant is in the pharmaceutical composition in an amount of about 0.01% w/w to about 95% w/w. In some embodiments, the surfactant is in the pharmaceutical composition in an amount of about 0.1% w/w to about 10% w/w.

In some embodiments, the suspending agent may be selected from the group consisting of gelatin, colloidal silica, crosslinked polyacrylic acid, polymethacrylic acid, polyhydroxyethyl methacrylic acid, hydroxypropyl methyl cellulose, sodium carboxymethyl cellulose, hyaluronic acid, chitosan, polycarbophil, pectin, copolymers of dextran, polyacrylamide, acacia, copolymer of caprolactone and ethylene oxide, carbopol 934, tragacanth, eudragit, polyvinyl pyrrolidone, polyacrylate and polyacrylate copolymer resins, celluloses and cellulose derivatives, for example, methyl-, ethyl- and propyl celluloses; hydroxyalkyl-celluloses, hydroxyl propyl celluloses, hydroxylpropylalkyl celluloses and the like including xanthan gum, polyvinyl resins, polyethylene glycol, polyethylene oxide, sorbitol, sucrose, xylitol, dextrose, fructose, maltitol, sugar, sodium alginate, and a combination thereof.

In some embodiments, the suspending agent is in the pharmaceutical composition in an amount of about 0.01% w/w, about 0.1% w/w, about 0.5% w/w, about 1% w/w, about 2% w/w, about 3% w/w, about 4% w/w, about 5% w/w, about 6% w/w, about 7% w/w, about 8% w/w, about 9% w/w, about 10% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w, about 85% w/w, about 90% w/w, about 95% w/w, or a range of any two of these values. In some embodiments, the suspending agent is in the pharmaceutical composition in an amount of about 1% w/w to about 20% w/w.

In some embodiments, the suspension comprises about 0.1% w/w to about 50% w/w of the active agent, about 0.01% w/w to about 10% w/w surfactant, about 0.1% w/w to about 20% w/w suspending agent, and about 0.1% w/w to about 95% w/w medium chain triglyceride. In some embodiments, the suspension does not include water. In some embodiments, the suspension further comprises water.

In some embodiments, the pharmaceutical composition further includes one or more pharmaceutically acceptable excipients selected from the group comprising of one or more preservatives/antioxidants, one or more solubilizers, one or more buffering agents, one or more chelating agents, one or more sweetening agents, one or more flavoring agents, one or more sweetness/flavor enhancing agents, or combination thereof. In some embodiments, the pharmaceutically acceptable excipient is in an amount of about 0.1% w/w, about 0.5% w/w, about 1% w/w, about 2% w/w, about 3% w/w, about 4% w/w, about 5% w/w, about 6% w/w, about 7% w/w, about 8% w/w, about 9% w/w, about 10% w/w, or a range of any two of these values.

Solubilizers are organic solvents used in liquid drug formulations to increase the solubility of poorly soluble substances and enhance the chemical stability of a drug. In some embodiments, the solubilizer may be selected from ethanol, propylene glycol, polyhydric alcohols such as concentrated glycerol, glycerol, polyvinyl alcohol, propylene glycol, ethylene glycol, or a combination thereof. In some embodiments, the solubilizer is ethanol. In some embodiments, the solubilizer is propylene glycol.

In some embodiments, the solubilizer may be in an amount of about 0.1% w/w, about 1% w/w, about 3% w/w, about 5% w/w, about 10% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, or a range of any two of these values. In some embodiments, the solubilizer may be in an amount of about 0.1% w/w to about 60% w/w. In some embodiments, the solubilizer may be in an amount of about 2% w/w.

Preservatives are compounds which are included in pharmaceutical dosage form to prevent the growth of microorganisms during the product's manufacture and shelf life. Examples of the suitable preservatives are, but not limited to, benzyl alcohol, chloro-butanol, chloro-cresol, alkyl esters of Paxaben, phenol, phenyl ethanol, benzoic acid, potassium sorbate, sodium benzoate and antimicrobial solvents like propylene glycol, chloroform, or a combination thereof.

Antioxidants are substances capable of inhibiting oxidation and that may be added to pharmaceutical products to prevent deterioration by oxidative processes. Examples of suitable antioxidants are but not limited to Butylatedhydroxyanisole (BHA), Butylatedhydroxy toluene (BHT), Sodium metabisulfite, Ascorbic acid, Alphatocopherol, Sodium edetate, or any combination thereof. In some embodiments, the antioxidant is BHT.

Buffering agents are compounds which provide stability and pH control to the pharmaceutical formulations. Examples of suitable buffering agents are but not limited to tris(hydroxymethyl)aminomethane (TRIS), triethanolamine, sodium acetate, sodium citrate, ammonium sulfate, sodium phosphate, disodium hydrogen phosphate, potassium citrate, citric acid monohydrate, trisodium citrate dehydrate, or a combination thereof.

Chelating agents are compounds which are used for drug stabilization, to maintain potency of active pharmaceutical ingredients and to stabilize colors and flavors. Examples of suitable chelating agents are but not limited to citric acid monohydrate, disodium edetate, dipotassium edetate, edetic acid, fumaric acid, malic acid, phosphoric acid, sodium edetate, tartaric acid, trisodium edetate, or a combination thereof.

Sweetening agents are compounds that impart sweetness and improve patient compliance through taste masking. Examples of the suitable sweetening agents are but not limited to sucralose, sucrose, acesulfame potassium, liquid glucose, glycerine, sorbitol, liquid maltitol, saccharin sodium, aspartame, or a combination thereof. In some embodiments, the sweetening agent is sucralose.

Flavoring agents are the compounds which are added to increase patient acceptance of the drug by masking the specific taste sensations. Examples of suitable flavoring agent are, but not limited to, essential oils including peppermint oil, orange oil or lemon oil, fruit flavor, peppermint flavor, strawberry flavor, tutti-fruity flavor, mint flavor, or a combination thereof. In some embodiments, the flavoring agent is a peppermint flavor.

In some embodiments, the pharmaceutical composition of embodiments herein is a liquid suspension. In some embodiments, the liquid suspension is suitable for oral administration.

In some embodiments, the pharmaceutical composition of embodiments herein is useful for the manufacture of a medicament. In one of the further embodiments, the pharmaceutical composition of embodiments herein is useful as a medicament.

In some embodiments, the active pharmaceutical ingredient may be administered in combination with one or more additional active pharmaceutical ingredients. In some embodiments, the pharmaceutical composition of embodiments herein may include an additional active pharmaceutical ingredient. In some embodiments, the pharmaceutical composition of embodiments herein may be administered in conjunction with, either concurrently or sequentially, with the additional active pharmaceutical ingredient.

Methods of Treatment

Some embodiments are directed to a methods of using the pharmaceutical composition of embodiments herein for the treatment of diseases or disorders. In some embodiments, the disease or disorder comprises cancer, multiple myeloma, cancers of the blood, myelodysplastic syndrome, Hodgkin's lymphoma, non-Hodgkin's lymphoma, chronic lymphosytic leukemia, solid tumor cancers, carcinoma of the pancreas, B-cell chronic lymphocytic leukemia, or a combination thereof, wherein the active pharmaceutical ingredient is lenalidomide.

In some embodiments, the disease or disorder comprises cancer, brain cancer, astrocytoma, glioblastoma, glioblastoma multiforme, anaplastic astrocytoma, melanoma, brain metastasis, brain metastasis of breast cancer, or a combination thereof, wherein the active pharmaceutical ingredient is temozolomide.

In some embodiments, a method of treating cancer in a subject in need thereof comprises administering to the subject the pharmaceutical composition of embodiments herein, wherein the active pharmaceutical ingredient is temozolomide.

In some embodiments, a method of treating multiple myeloma in a subject in need thereof comprises administering to the subject the pharmaceutical composition of embodiments herein, wherein the active pharmaceutical ingredient is lenalidomide.

In some embodiments, a method of treating a myelodysplastic syndrome in a subject in need thereof comprises administering to the subject the pharmaceutical composition of embodiments herein, wherein the active pharmaceutical ingredient is lenalidomide.

In some embodiments, a method of treating astrocytoma in a subject in need thereof comprises administering to the subject the pharmaceutical composition of embodiments herein, wherein the active pharmaceutical ingredient is temozolomide.

In some embodiments, a method of treating glioblastoma multiforme in a subject in need thereof comprises administering to the subject the pharmaceutical composition of embodiments herein, wherein the active pharmaceutical ingredient is temozolomide.

Rapid dissolution of an administered active pharmaceutical ingredient is preferable, as faster dissolution generally leads to greater bioavailability and faster onset of action. To improve the dissolution profile and bioavailability of an active pharmaceutical ingredient, it would be useful to increase dissolution of the active pharmaceutical ingredient used so that it could attain a level close to 100% dissolution of the drug substance.

The liquid pharmaceutical compositions of embodiments herein comprising the active pharmaceutical ingredient or derivative thereof, exhibit improved or comparable pharmacokinetic profiles as compared to marketed or known compositions of the same active pharmaceutical ingredient or derivative thereof. For example, the Cmax and/or AUC of the liquid pharmaceutical compositions of disclosed herein can be greater than or substantially equal to the Cmax and/or AUC for known or marketed compositions, e.g. solid formulations, administered at the same dose. In addition, the Tmax of the liquid compositions of the present invention can be lower than or substantially equal to that obtained for a known or marketed compositions, administered at the same dose. In addition, combinations of an improved or comparable Cmax, AUC and Tmax profile can be exhibited by the liquid compositions of the invention, as compared to known or marketed compositions. In further aspects, the liquid compositions of the present invention may result in minimal different absorption levels when administered under fed as compared to fasting conditions.

The liquid compositions of embodiments herein exhibit in comparative pharmacokinetic testing with marketed or known formulations, administered at the same dose, a Tmax not greater than about 90%, not greater than about 80%, not greater than about 70%, not greater than about 60%, not greater than about 50%, not greater than about 30%, not greater than about 25%, not greater than about 20%, not greater than about 15%, not greater than about 10%, or not greater than about 5% of the Tmax exhibited by the marketed or known formulation.

In some embodiments, the liquid compositions of embodiments herein exhibit in comparative pharmacokinetic testing with marketed or known formulation, administered at the same dose, a Cmax which is at least about 50%, at least about 100%, at least about 200%, at least about 300%, at least about 400%, at least about 500%, at least about 600%, at least about 700%, at least about 800%, at least about 900%, at least about 1000%, at least about 1100%, at least about 1200%, at least about 1300%, at least about 1400%, at least about 1500%, at least about 1600%, at least about 1700%, at least about 1800%, or at least about 1900% greater than the Cmax exhibited by the marketed or known formulation.

In one of the further aspects, the liquid compositions of embodiments herein exhibit in comparative pharmacokinetic testing with marketed or known formulation, administered at the same dose, an AUC which is at least about 25%, at least about 50%, at least about 75%, at least about 100%, at least about 125%, at least about 150%, at least about 175%, at least about 200%, at least about 225%, at least about 250%, at least about 275%, at least about 300%, at least about 350%, at least about 400%, at least about 450%, at least about 500%, at least about 550%, at least about 600%, at least 5 about 750%, at least about 700%, at least about 750%, at least about 800%, at least about 850%, at least about 900%, at least about 950%, at least about 1000%, at least about 1050%, at least about 1100%, at least about 1150%, or at least about 1200% greater than the AUC exhibited by the marketed or known formulation.

In some embodiments, the Tmax of the active pharmaceutical ingredient or salt thereof used for the preparation of the liquid composition of embodiments herein, when assayed in the plasma of the mammalian subject, is less than about 6 to about 8 hours. In other aspects of the invention, the Tmax of the active pharmaceutical ingredient or salt thereof is less than about 6 hours, less than about 5 hours, less than about 4 hours, less than about 3 hours, less than about 2 hours, less than about 1 hour, or less than about 30 minutes after administration.

In some aspects, the liquid compositions of embodiments herein exhibit improved or comparable bioavailability as compared to known or marketed compositions.

Methods of Preparing Formulation

The oral pharmaceutical suspension of embodiments above may be prepared by the following steps irrespective to order of addition, including, but not limited to,:
- A) Add suspending agent, surfactant, anti-oxidant, preservative, sweetener, flavoring agent one by one till it dissolve or disperse;
- B) Add API and mix till it disperses;
- C) Make volume up to desired batch size.

The embodiments illustrating the method and materials used may be further understood by reference to the following non-limiting examples.

Example 1: Method of Preparing Temozolomide Suspension

A suspension of temozolomide is prepared using the method outlined below:
- a. Disperse suspending agent in vehicle
- b. Disperse API in mixture of step a
- c. Dissolve antioxidant and sweetener in solubilizer separately and add to mixture of step b
- d. Add flavor and mix till it is dispersed
- e. Make up volume to final volume The final suspension formulation for temozolomide is as follows:

TABLE 4

TEMOZOLOMIDE FORMULATION

| Sr No | Name of Ingredients | Formula mg/ml |
|---|---|---|
| 1 | Temozolomide | 30.0 |
| 2 | Ethanol | 40 |
| 3 | BHT (Butoxylatedhydroxytoluene) | 0.15 |
| 4 | Sucralose | 1 |
| 5 | Colloidal silicone dioxide | 12.5 |
| 6 | Peppermint flavor | Q.S. |
| 7 | Labrasol | 30 |
| 8 | Medium chain triglyceride miglyol (kollisolv 70) | Q.S. |

Those who are skilled in the art can also understand that some variations in the herein described processes for the preparation of liquid compositions of the present invention can be adopted which are well within the skills of the skilled artisan. One can change sequences of the steps in the above mentioned process for the purposes of suitability and convenience without affecting the quality and characteristics of the resulting product.

Those who are reasonably skilled in the art can easily understand that similar liquid formulations using other active chemotherapeutic agents, including without limitation those mentioned in the above paragraphs with other suitable excipients, also mentioned in the foregoing paragraphs may be prepared in the above mentioned formulas using above mentioned processes for preparation. Such other examples of compositions and processes of preparation thereof are also within the ambit of the invention disclosed and claimed in the present application.

Example 2: Method of Preparing Lenalidomide Suspension

A suspension of lenalidomide is prepared using the method outlined below:
- a. Disperse suspending agent in vehicle
- b. Disperse API in mixture of a step a
- c. Dissolve antioxidant and sweetener in solubilizer separately and add to mixture of step b
- d. Add flavor and mix till it is dispersed
- e. Make up volume to final volume The final suspension formulation for lenalidomide is as follows:

TABLE 5

LENALIDOMIDE FORMULATION

| Sr. No. | Ingredients | Role of Ingredients | Formula % Percentage | Formula (mg/mL) |
|---|---|---|---|---|
| 1 | Lenalidomide | Active ingredient | 0.500 | 5.00 |
| 2 | Colloidal silicone dioxide (Aerosil 200) | Suspending agent | 1.5 | 15 |
| 3 | Caprylocaproyl macrogo 8 glycerides (LABRASOL) | Surfactant | 5.000 | 50.00 |
| 4 | Ethanol absolute | Solubilizer | 2.000 | 20.00 |
| 5 | Butylated hydroxy toluene | Antioxidant | 0.015 | 0.15 |
| 6 | Sucralose | Sweetener | 0.100 | 1.00 |
| 7 | Frozen peppermint flavour | Flavoring agent | 0.200 | 2.00 |
| 8 | Medium chain triglyceride (Kollisolv MCT 70) | Vehicle | Q.S to 100 | Q.S to 1 ml |

Those who are skilled in the art can also understand that some variations in the herein described processes for the preparation of liquid compositions of the present invention can be adopted which are well within the skills of the skilled artisan. One can change sequences of the steps in the above mentioned process for the purposes of suitability and convenience without affecting the quality and characteristics of the resulting product.

Those who are reasonably skilled in the art can easily understand that similar liquid formulations using other active chemotherapeutic agents, including without limitation those mentioned in the above paragraphs with other suitable excipients, also mentioned in the foregoing paragraphs may be prepared in the above mentioned formulas using above mentioned processes for preparation. Such other examples of compositions and processes of preparation thereof are also within the ambit of the invention disclosed and claimed in the present application.

Example 3: Stability and Dissolution

The oral liquid pharmaceutical composition prepared according to Example 1 exhibits unexpected stability profile when tested after three (3) months under the conditions 40° C./25 RH and 25° C./40 RH. The liquid composition according to the present disclosure possesses low amounts of impurities and highest degree of purity. The results of the stability tests conducted are summarized in the table below:

TABLE 6

STABILITY AND DISSOLUTION

| Sr. No | Test parameters | Condition | Initial | 40° C./ 25% RH 3M | 25° C./ 40% RH 3M |
|---|---|---|---|---|---|
| 1 | Description | | white to light pink color suspension | White to offwhite suspension | Light pink colour suspension | Off white suspension |

TABLE 6-continued

STABILITY AND DISSOLUTION

| Sr. No | Test parameters | Condition | Initial | 40° C./ 25% RH 3M | 25° C./ 40% RH 3M |
|---|---|---|---|---|---|
| 2 | Assay of Temozolamide | 90.0% to 110.0% | 103.00% | 102.30% | 101.60% |
| 3 | Assay of BHT | 80.0% to 110.0% | 96.50% | 92.50% | 94.00% |
| 4 | Assay of Ethanol | 60.0% to 110.0% | 96.20% | 90.20% | 89.60% |
| 5 | Related Substances | | | | |
|  | Impurity -A | NMT 0.2% | ND | ND | ND |
|  | Impurity -B | NMT 0.2% | ND | ND | ND |
|  | impurity- E | NMT 0.2% | ND | 0.11% | 0.01% |
|  | Single maximum unknown impurity | NMT 0.2% | ND | 0.02% | ND |
|  | Total impurities | NMT 2.0% | 0.00% | 0.13% | 0.01% |
| 6 | Dissolution- % Drug dissolved in purified water | 10 min | 72.1 | 69 | 74.1 |
|  |  | 15 min | 83.4 | 81.4 | 89.2 |
|  |  | 20 min | 89.4 | 91.1 | 98.1 |
|  |  | 30 min | 97.8 | 98.8 | 102 |
|  |  | 45 min | 102.4 | 99.4 | 102.1 |

Although embodiments herein has been described in considerable detail with reference to certain preferred embodiments thereof, other versions are possible. Therefore, the spirit and scope of the appended claims should not be limited to the description and the preferred versions contained within this specification.

The invention claimed is:

1. A non-aqueous liquid pharmaceutical suspension comprising:
    lenalidomide in an amount of about 5 mg/ml;
    a polyethoxylated sorbitan ester as a surfactant in an amount of about 1% w/w to about 2% w/w;
    a colloidal silica as a suspending agent in an amount of about 1% w/w to about 1.25% w/w;
    one or more pharmaceutically acceptable excipients; and
    a medium chain fatty acid triglyceride as a vehicle.

2. The non-aqueous liquid pharmaceutical suspension of claim 1, wherein the polyethoxylated sorbitan ester as a surfactant is present in an amount of from about 2% w/w.

3. The non-aqueous liquid pharmaceutical suspension of claim 1, wherein the colloidal silica as a suspending agent is present in an amount of from about 1.15% w/w.

4. The non-aqueous liquid pharmaceutical suspension of claim 1, wherein the one or more pharmaceutically acceptable excipients is selected from the group consisting of a sweetener, a flavoring agent, and a preservative.

5. The non-aqueous liquid pharmaceutical suspension of claim 1, wherein the one or more pharmaceutically acceptable excipients is present in an amount of from about 0.1% w/w to about 10% w/w.

6. The non-aqueous liquid pharmaceutical suspension of claim 1, wherein the medium chain fatty acid triglyceride as a vehicle is present in an amount of from about 70% w/w to about 99% w/w.

7. The non-aqueous liquid pharmaceutical suspension of claim 1, wherein the medium chain fatty acid triglyceride as a vehicle is present in an amount of from about 90% w/w to about 95% w/w.

8. A method of treating a disease in a human in need thereof, the method comprising administering a therapeutically effective amount of the non-aqueous liquid pharmaceutical suspension of claim 1 to the human;
    wherein the disease is selected from multiple myeloma, myelodysplastic syndrome, and a lymphoma.

9. A non-aqueous liquid pharmaceutical suspension, comprising:
    lenalidomide in an amount of about 0.5% w/w;
    a polyethoxylated sorbitan ester as a surfactant in an amount of from about 1% w/w to about 2% w/w;
    a colloidal silica as a suspending agent in an amount of from about 1% w/w to about 1.25% w/w;
    one or more pharmaceutically acceptable excipients selected from the group consisting of a sweetener, a flavoring agent, and a preservative; and
    a medium chain fatty acid triglyceride as a vehicle in an amount of from about 70% w/w to about 99% w/w.

10. A method of treating a disease in a human in need thereof, the method comprising administering a therapeutically effective amount of the non-aqueous liquid pharmaceutical suspension of claim 9 to the human;
    wherein the disease is selected from multiple myeloma, myelodysplastic syndrome, and a lymphoma.

11. A non-aqueous liquid pharmaceutical suspension, consisting essentially of:
    lenalidomide in an amount of about 0.5% w/w;
    a polyethoxylated sorbitan ester as a surfactant in an amount of from about 1% w/w to about 2% w/w;
    a colloidal silica as a suspending agent in an amount of from about 1% w/w to about 1.25% w/w;
    one or more pharmaceutically acceptable excipients selected from the group consisting of a sweetener, a flavoring agent, a sweetness/flavor enhancing agent, and a preservative; and
    a medium chain fatty acid triglyceride as a vehicle in an amount of from about 70% w/w to about 99% w/w.

12. A method of treating a disease in a human in need thereof, the method comprising administering a therapeutically effective amount of the non-aqueous liquid pharmaceutical suspension of claim 11 to the human;
    wherein the disease is selected from multiple myeloma, myelodysplastic syndrome, and a lymphoma.

13. A non-aqueous liquid pharmaceutical suspension, consisting of:
    lenalidomide in an amount of about 0.5% w/w;
    a polyethoxylated sorbitan ester as a surfactant in an amount of from about 1% w/w to about 2% w/w;
    a colloidal silica as a suspending agent in an amount of from about 1% w/w to about 1.25% w/w;
    one or more pharmaceutically acceptable excipients selected from the group consisting of a sweetener, a flavoring agent, and a preservative; and
    a medium chain fatty acid triglyceride as a vehicle in an amount of from about 70% w/w to about 99% w/w.

14. A method of treating a disease in a human in need thereof, the method comprising administering a therapeutically effective amount of the non-aqueous liquid pharmaceutical suspension of claim 13 to the human;
    wherein the disease is selected from multiple myeloma, myelodysplastic syndrome, and a lymphoma.

* * * * *

UNITED STATES PATENT AND TRADEMARK OFFICE
CERTIFICATE OF CORRECTION

PATENT NO. : 12,303,504 B2  
APPLICATION NO. : 17/274432  
DATED : May 20, 2025  
INVENTOR(S) : Patel et al.

Page 1 of 2

It is certified that error appears in the above-identified patent and that said Letters Patent is hereby corrected as shown below:

On the Title Page

Column 2, Abstract (item (57)), Line 11, "vinoralbine," should read -- vinorelbine, --.

In the Specification

Column 1, Line 30, "vinoralbine," should read -- vinorelbine, --;

Column 1, Line 44, "oilarachis" should read -- oil, arachis --; and

Column 1, Line 66, "hydroginated" should read -- hydrogenated --.

Column 2, Line 8, "polyvinylacetate-polyethyleneglycol" should read -- polyvinyl acetate-polyethylene glycol --;

Column 2, Line 22, "hydroxylpropylalkyl" should read -- hydroxypropyl alkyl --; and Column 2, Line 37, "lymphosytic" should read -- lymphocytic --.

Column 6, Line 35, "vinoralbine," should read -- vinorelbine, --.

Column 7, Line 55, "oilarachis" should read -- oil, arachis --.

Column 8, Line 27, "hydroginated" should read -- hydrogenated --; and

Column 8, Line 36, "polyvinylacetate-polyethyleneglycol" should read -- polyvinyl acetate-polyethylene glycol --.

Column 9, Line 20, "hydroxylpropylalkyl" should read -- hydroxylpropyl alkyl --.

Signed and Sealed this  
Eighth Day of July, 2025

Coke Morgan Stewart  
*Acting Director of the United States Patent and Trademark Office*

CERTIFICATE OF CORRECTION (continued)
U.S. Pat. No. 12,303,504 B2

Column 10, Line 16, "Paxaben," should read -- Paraben, --;

Column 10, Lines 23-24, "Butylatedhydroxyanisole" should read -- Butylated Hydroxyanisole --;

Column 10, Line 24, "Butylatedhydroxy toluene" should read -- Butylated Hydroxytoluene --; and Column 10, Line 25, "Alphatocopherol," should read -- Alpha-tocopherol, --.

Column 11, Line 16, "lymphosytic" should read -- lymphocytic --.

Column 13, Line 4, "limited to,:" should read -- limited to: --;

Column 13, Table 4, Line 35, "(Butoxylatedhydroxytoluene)" should read -- (Butylated Hydroxytoluene) --; and Column 13, Line 65, "of a step a" should read -- of step a --.

Column 14, Table 5, Line 17, "macrogo 8" should read -- macrogol 8 --.

Column 15, Table 6, Line 8, "Temozolamide" should read -- Temozolomide --;

In the Claims

Column 15, Claim 1, Line 36, "5 mg/ml;" should read -- 5 mg/mL; --;

Column 15, Claim 2, Line 44, "of from about 2% w/w" should read -- of about 2% w/w --; and Column 15, Claim 3, Line 47, "of from about 1.15%" should read -- of about 1.15% w/w --.